(12) United States Patent
Lynch (10) Patent No.: US 9,987,186 B1
(45) Date of Patent: Jun. 5, 2018

(54) SPLINTED COMPRESSION BANDAGE

(71) Applicant: Allie Lynch, St. John's (CA)

(72) Inventor: Allie Lynch, St. John's (CA)

( * ) Notice: Subject to any disclaimer, the term of this patent is extended or adjusted under 35 U.S.C. 154(b) by 330 days.

(21) Appl. No.: 14/566,201

(22) Filed: Dec. 10, 2014

Related U.S. Application Data (60) Provisional application No. 61/914,121, filed on Dec. 10, 2013.

(51) Int. Cl.
*A61F 13/00* (2006.01)
*A61F 5/058* (2006.01)
*A61H 1/00* (2006.01)

(52) U.S. Cl.
CPC ............. *A61H 1/008* (2013.01); *A61F 5/058* (2013.01); *A61F 13/00021* (2013.01); *A61F 13/00029* (2013.01); *A61F 2013/00234* (2013.01)

(58) Field of Classification Search
CPC ........ A61F 5/058; A61F 5/05; A61F 5/05825; A61F 5/05875; A61F 5/01; A61F 5/0102; A61F 5/0104; A61F 5/0106; A61F 5/0118; A61F 13/00038; A61F 13/0206; A61F 13/0246; A61F 13/04; A61F 13/08; A61F 13/10; A61F 13/12; A61F 13/104; A61F 13/00035; A61F 13/00021; A61F 13/0273; A61F 13/00025; A61F 13/00029; A61F 2013/000119; A61F 2013/00604; A61F 2013/00608; A61F 2013/00234; A61F 2013/00936; A61F 5/02; A61H 1/008; A61K 9/70; A41C 1/02; A41C 3/00

USPC ...... 128/845, 846, 857, 858; 602/53, 13, 46, 602/26, 41, 42, 64, 6–8, 20–23, 30, 44, 602/48, 60–62, 70, 75–76; 442/229, 7, 8, 442/182, 228; 424/443

See application file for complete search history.

(56) References Cited

U.S. PATENT DOCUMENTS

| | | | | |
|---|---|---|---|---|
| 543,069 | A | * 7/1895 | De Ver | A41C 1/20 2/257 |
| 2,933,083 | A | * 4/1960 | Kozdas | A61F 13/0246 128/888 |
| 2,957,475 | A | * 10/1960 | Drake | A61F 13/04 602/5 |
| 3,373,741 | A | * 3/1968 | Hill | A61F 13/04 206/440 |
| 3,901,225 | A | 8/1975 | Sconce | |
| 4,161,175 | A | * 7/1979 | Bentele | A61F 5/05875 602/6 |
| 4,207,885 | A | * 6/1980 | Hampton | A61F 13/00021 139/419 |
| 4,676,233 | A | * 6/1987 | Scheinberg | A61F 5/055 128/DIG. 23 |
| 4,872,448 | A | 10/1989 | Johnson, Jr. | |
| 5,314,455 | A | 5/1994 | Johnson, Jr. et al. | |
| 5,507,721 | A | 4/1996 | Shippert | |
| 5,628,723 | A | 5/1997 | Grau | |
| 5,643,315 | A | 7/1997 | Daneshvar | |

(Continued)

*Primary Examiner* — Keri J Nelson
(74) *Attorney, Agent, or Firm* — Aaron R. Cramer; Cramer Patent & Design, PLLC (57) ABSTRACT

A compression-type bandaging incorporates parallel wire members operatively spaced within a pair of elastic layers such that the wire members can be shaped to conform to the limb or area that is under compression and further provide a semi-rigid splint function. Each elastic layer includes a lattice structure of threads.

20 Claims, 5 Drawing Sheets (56) References Cited

U.S. PATENT DOCUMENTS

| | | | | |
|---|---|---|---|---|
| 5,833,636 | A * | 11/1998 | Yokoi | A61F 5/05825 |
| | | | | 602/5 |
| 6,171,271 | B1 | 1/2001 | Hörnberg | |
| 6,762,337 | B2 | 7/2004 | Boukanov et al. | |
| 8,303,527 | B2 | 11/2012 | Joseph | |
| 9,039,643 | B2 * | 5/2015 | Bolla | A61F 5/05825 |
| | | | | 602/5 |
| 2002/0061692 | A1 * | 5/2002 | Steckmann | B32B 15/02 |
| | | | | 442/229 |
| 2004/0014384 | A1 * | 1/2004 | Sloot | B32B 27/12 |
| | | | | 442/131 |
| 2005/0043664 | A1 * | 2/2005 | Reaux | A61F 13/04 |
| | | | | 602/63 |
| 2009/0099497 | A1 * | 4/2009 | Jung | A61F 13/00038 |
| | | | | 602/76 |
| 2009/0143709 | A1 * | 6/2009 | Naumann | A61F 13/145 |
| | | | | 602/44 |
| 2010/0305535 | A1 * | 12/2010 | Leeming | A61F 13/069 |
| | | | | 604/367 |

* cited by examiner

SPLINTED COMPRESSION BANDAGE

RELATED APPLICATIONS

The present invention is a continuation-in-part of, was first described in, and claims the benefit of U.S. Provisional Application No. 61/914,121, filed Dec. 10, 2013, the entire disclosures of which are incorporated herein by reference.

FIELD OF THE INVENTION

The present invention relates generally to a compression bandage having flexible members incorporated throughout that enable the bandage to dually serve as a compression bandage and a splint.

BACKGROUND OF THE INVENTION

During emergency medical treatment, it is a common occurrence to apply a splint. Such splints are often used to immobilize an extremity in response to an injury, or prevent even further injury. They are frequently used in response to broken bones, sprains, and the like. In some cases, they may even be applied around torsos when dealing with spinal cord injuries. Such splints typically comprise a compression bandage and an immobilization device. The elastic nature of bandage ensures that the splint remains tight, yet not overly restrictive. The immobilizing device is a rigid member, which can be as simple as a piece of wood or as complex as a configurable plastic channel. In any case, the bandage and the immobilizing device are two (2) separate pieces, which often requires two (2) or more people to apply. Additionally, the immobilizing device frequently requires cutting or customization to be applicable to an individual patient, which might consume valuable time in exigent circumstances. Accordingly, there exists a need for a means by which the components needed to produce a splint can be combined into one (1) piece. The development of the present invention fulfills this need.

SUMMARY OF THE INVENTION

It is therefore an object of the present invention to provide such a bandage having an elastic layer composed of a plurality of first threads arranged in a first direction and a plurality of second threads running in a second direction. In at least one (1) embodiment, the first threads and second threads exhibit different stretching capabilities in order to produce a compressive force for the bandage. Moldable wires are bound to the surface of the elastic layer to assist in molding the bandage to a specific body location. In at least one (1) embodiment, the wires are arranged in a parallel configuration.

Another object of the present invention is to provide such a bandage as described above, but further having a plurality of third threads arranged in a third direction and a plurality of fourth threads running in a fourth direction. In at least one (1) embodiment, the direction of the first and third threads are substantially parallel to each other. In at least one (1) embodiment, the direction of the second and fourth threads are substantially parallel to each other. In at least one (1) embodiment, the third threads and fourth threads exhibit different stretching capabilities, similar as above in regards to the first and second threads, in order to produce a compressive force for the bandage. Moldable wires are bonded between the first and second elastic layers.

Yet another object of the present invention provides for each distal end of each moldable wire to be shaped in a torus to assist in positioning of the wire within the elastic layers prior to bonding with the adhesive and to eliminate unintended puncture of the elastic layers or of the patient.

Yet another object of the present invention provides for a reinforcement strip affixed to edges of the bandage and configured to cover adhered edges of the first and second elastic layers.

Still yet another object of the present invention is to provide a gauze pad is affixed to an outer surface of said bandage via an adhesive. In at least one (1) embodiment, an anti-bacterial non-stick ointment is disposed on a surface of the gauze pad.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY 10 splinted compression bandage
20 first elastic layer
30 second elastic layer
35 hem
40 adhesive
50 moldable wire
60 first thread
70 first direction
80 second thread
90 second direction
100 torus
110 gauze substrate
115 pronged clip
120 patient
125 extremity

DETAILED DESCRIPTION OF THE PREFERRED EMBODIMENT

Figure 3:
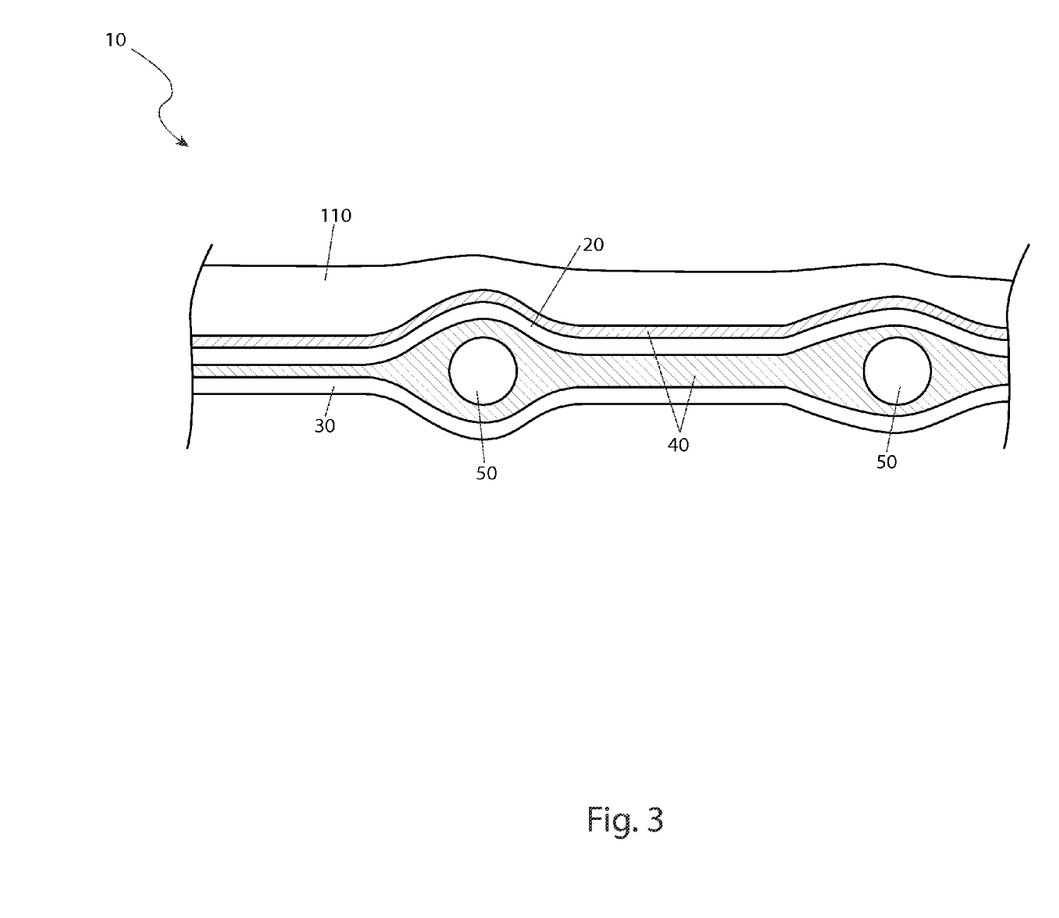
FIG. 3 is a side view of the device 10, in accordance with the preferred embodiment of the present invention.
Figure 4:
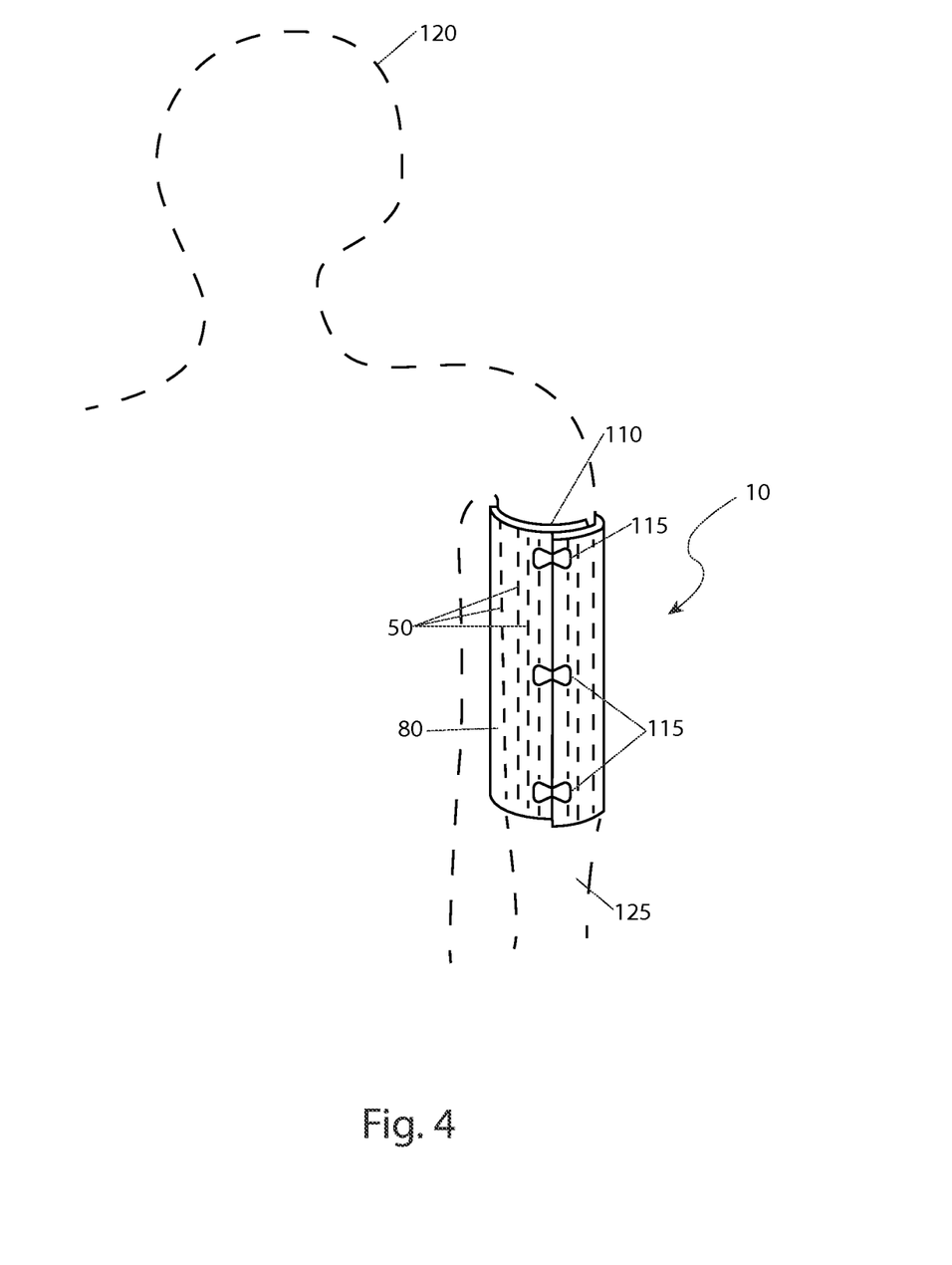
FIG. 4 is an environmental view of the device 10 depicting application to an extremity portion 125 of a patient 120, in accordance with the preferred embodiment of the present invention; and, FIG. 5 is a perspective view of an alternate splint compression bandage 10 showing a cut away view revealing the various components of the device 10, in accordance with the preferred embodiment of the present invention
Figure 5:
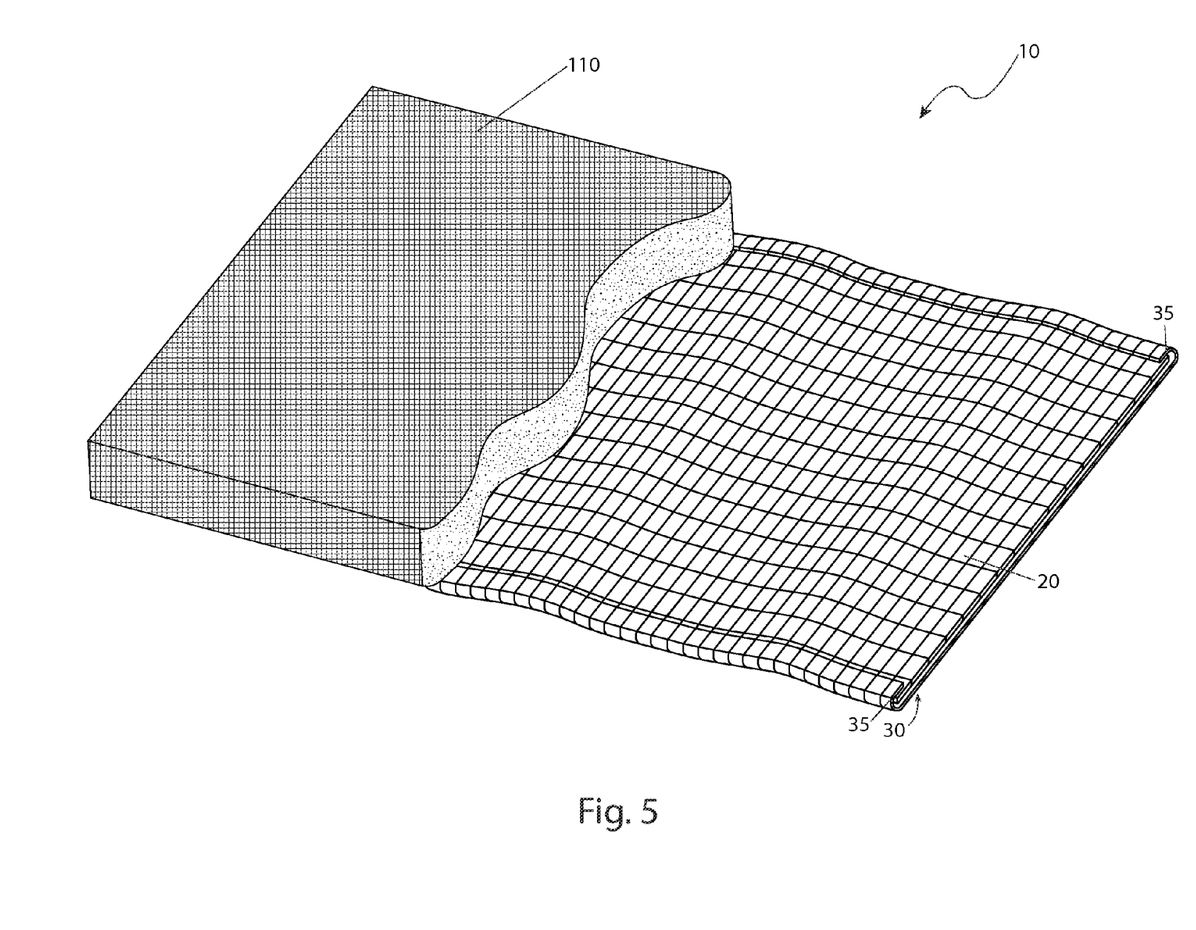

The best mode for carrying out the invention is presented in terms of its preferred embodiment, herein depicted within FIGS. 1 through 4, and in terms of an alternate embodiment, herein depicted in FIG. 5. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one (1) of the referenced items.

The present invention describes a splinted compression bandage (herein referred to as the "device") 10, which has a plurality of moldable wires 50 sandwiched between elastic layers 20, 30 to enable the device 10 to serve the dual function of a compression bandage and a splint.

Figure 1:
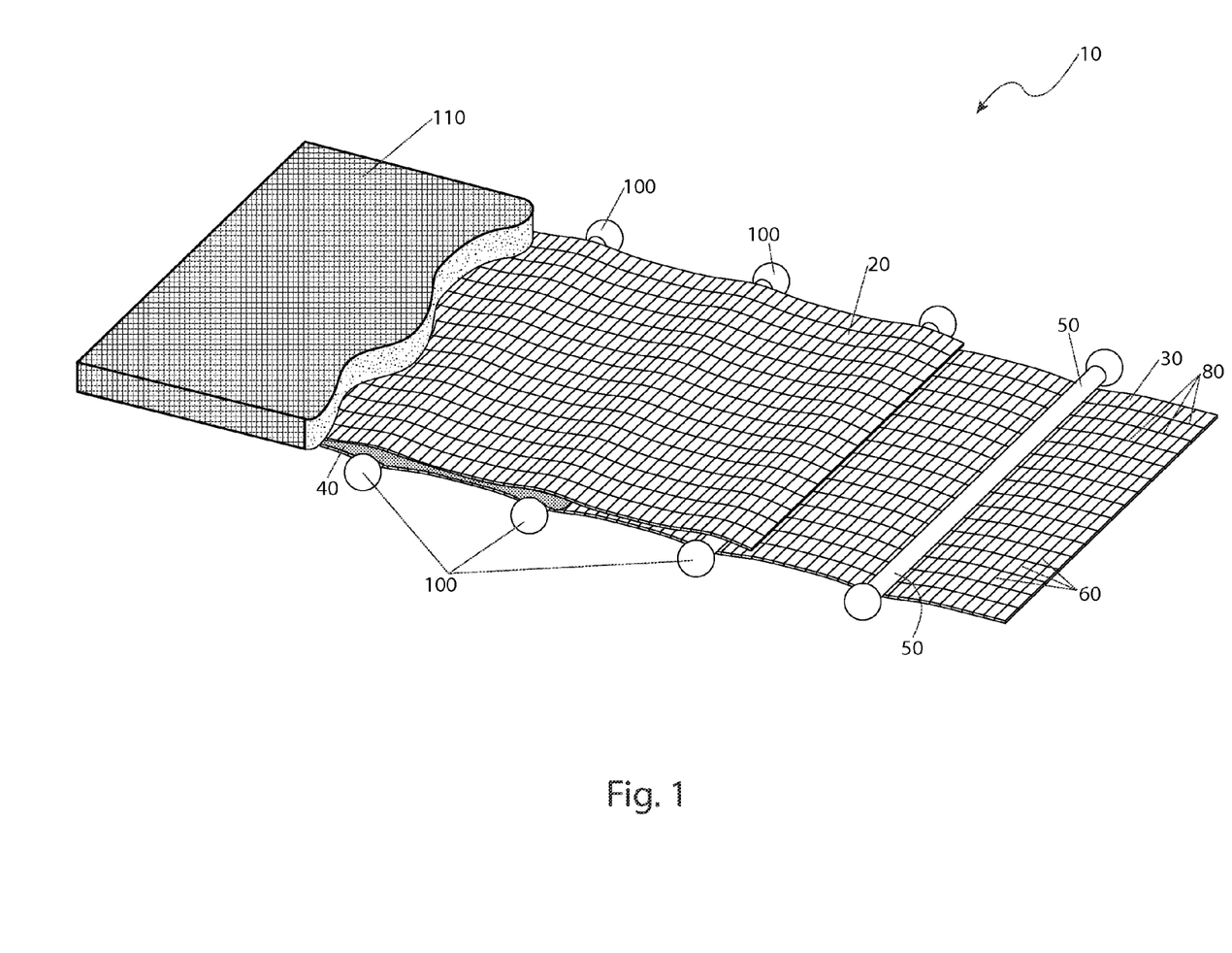
FIG. 1 is a perspective view of a splinted compression bandage 10 showing a cut away view revealing the various components of the device 10, in accordance with the preferred embodiment of the present invention.
Figure 2:
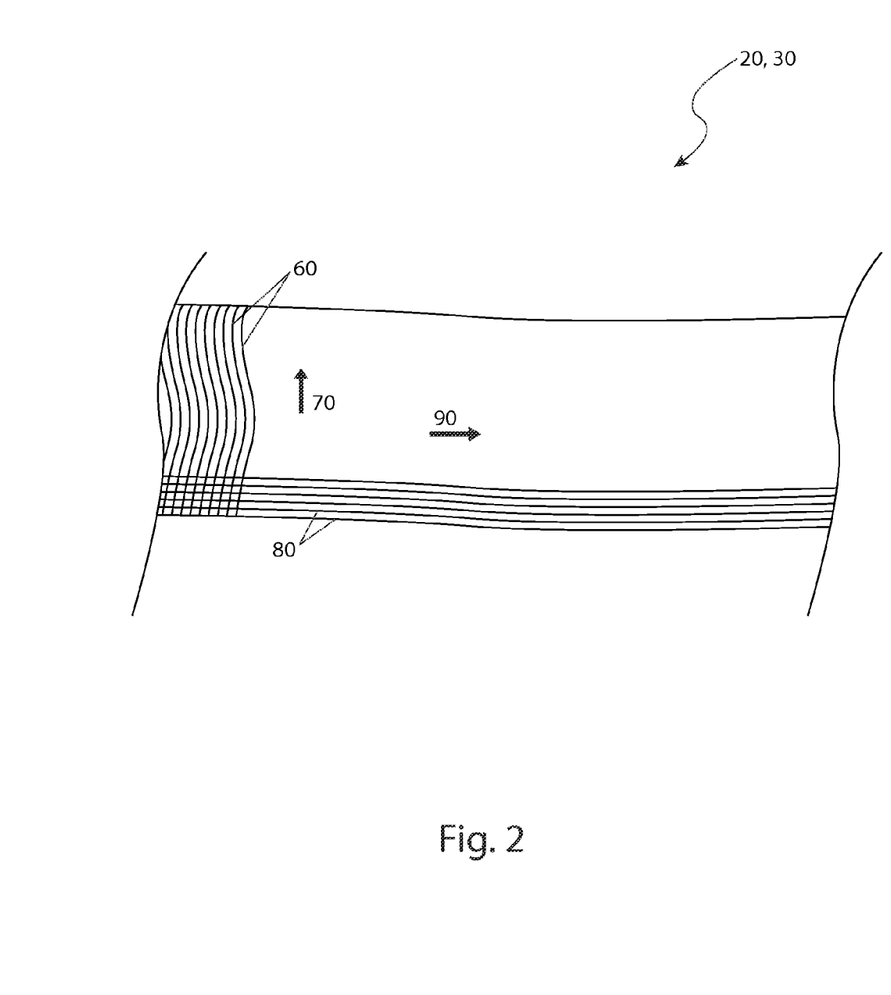
FIG. 2 is a top view of an elastic layer 20, 30 of the device 10 as it would be constructed in a woven fashion, in accordance with the preferred embodiment of the present invention.

Referring now to FIGS. 1 and 2, a perspective view of the device 10 showing a cut away view revealing the various components of the device 10, and a top view of an elastic layer 20, 30 as it would be constructed in a woven fashion, in accordance with the preferred embodiment of the present invention, are disclosed. The device 10 comprises a first elastic layer 20 and a second elastic layer 30 bonded together with an adhesive 40 (also see FIG. 3). Additionally, a plurality of individual moldable wires 50 are held in place within an adhesive layer 40 and between the elastic layers 20, 30. The wires 50 are positioned in a general parallel manner with respect to each other, and are generally evenly spaced from each other throughout the entire device 10. In use, the device 10 is wrapped around a body portion or extremity 125 of a patient 120 in a longitudinal direction and the wires 50 are molded to conform to the shape and contours of the body portion or extremity 125 about which they are wrapped so as to form a rigid cylindrical enclosure that can be used to keep injured body parts aligned. It is envisioned for the device 10 to be made available in multiple widths and lengths for splinting applications ranging from fingers to body torsos (see FIG. 4).

Each elastic layer 20, 30 provides an elongated elastic textile member exhibiting a compressive force when extended and installed upon an extremity 125 of the patient 120. It is envisioned for each elastic layer 20, 30 to comprise an arrangement of woven threads 60, 80 forming a lattice structure, where each first thread 60 is woven in a first direction 70 and each second thread 80 is woven in a second direction 90. Each first thread 60 exhibits a stretch capability that is less than that of each second thread 80 so that the device 10 may be stretched via the second direction 90 to be wrapped circumferentially about a body extremity 125, but maintain stretch resistance in the first direction 70 to provide adequate support. The differential stretch capability ratio between the first and second threads 60, 80 provides the compressive force and flexibility necessary for a compression bandage. Therefore, in use, of the device 10 is wrapped about a body portion or extremity 125 such that each first thread 60 is generally perpendicular to the longitudinal length of the extremity 125 and each second thread 80 is generally parallel to the longitudinal length of the extremity 125; however, it is envisioned that other applications might dictate other wrapping configurations. It is further envisioned for various lattice configurations and stretch capability ratios between the first 60 and second 80 threads to be used to achieve the desired level of applicability ranging from short-term compression applications to long term compression applications.

Referring now to FIG. 3, a side view of the device 10, in accordance with the preferred embodiment of the present invention, is disclosed. A plurality of moldable wires 50 are disposed between each layer 20, 30. Each wire 50 is preferably made using steel and exhibiting adequate strength and toughness to undergo plastic deformation repeatedly before material fatigue occurs. Each wire 50 is arranged in a substantially parallel manner with respect to each other, and may be set in various directional arrangements with respect to the first and second threads 60, 70; however, it is envisioned for each wire 50 to be situated substantially parallel to each first thread 60, as shown in FIG. 1.

In constructing the device 10, the first elastic layer 20 is laid flat, each wire 50 is placed on top of the first elastic layer 20 and arranged in accordance with a desired application of the device 10. Next, an adhesive 40 is applied and the second elastic layer 30 is placed on top of the first elastic layer 20, thereby sandwiching the wires 50 within. The adhesive 40 is used to bind the surfaces of each elastic layer 20, 30 together and resist separation of each layer 20, 30 as well as from the wires 50 contained within. The adhesive 40 exhibits resilient properties so as to maintain binding while the device 10 is being manipulated. It is preferred for each wire 50 to be completely encased with the elastic layer 20, 30; however, the configuration may be such that distal ends of each wire protrude from sides of the device 10. In the illustrated embodiment, each distal end of each wire 50 is provided with a torus 100 to assist with maintaining each wire 50 in place, and to obviate injury due to sharp or pointed edges of each wire 50.

The embodiment of the device 10 illustrated here utilizes a gauze substrate 110 being disposed on the first elastic layer 20 using additional adhesive 40, to absorb blood and discharge from a wound that the device 10 may cover when applied. However, it is understood that the gauze substrate 110 may be applied to the second elastic layer 30 as well as to both elastic layers 20, 30 based upon particular applications of the device 10. It is further envisioned for the gauze substrate 110 to be provided with applied or pre-applied medicinal, antibacterial, and/or non-stick substances, as needed based upon a particular wound type.

It is envisioned for the device 10 to be packaged in a rolled state where it is rolled about an axis defined by a wire 50. When use is required, the device 10 is unrolled and then wrapped about an extremity 125 so that each first thread 60 and each wire 50 are generally perpendicular to the longitudinal length of the extremity 125, and each second thread 80 is generally parallel to the longitudinal length of the extremity 125. The device 10 is wrapped about the extremity 125 a number of times and in a configuration dictated by the situation. As the device 10 is wrapped, an operator begins to mold the wires 50 so as to conform to the extremity 125 about which the device 10 is being wrapped and to create an overall shape that will be conducive to the healing and therapeutic functioning of the extremity 125.

Referring now to FIG. 4, an environmental view of the device 10 depicting application to an arm portion of a patient 120, in accordance with the preferred embodiment of the present invention, is disclosed. An embodiment of the device 10 is illustrated here being utilized to stabilize an arm of a patient 120; however, it is understood that the height and width dimensions of the device 10 may vary so as to correspond to, and provide like treatment for different portions of the patient's bodice such as leg, torso, or other portions, without deviating from the teachings of the invention, and as such should not be interpreted as a limiting factor. It is envisioned that the device 10 may be wrapped around the body portion or extremity 125 one (1) or more times to form a desired number of layers so as to obtain a desired amount of compressive support to the body portion or extremity 125. Furthermore, it is envisioned that any unused portion of the device 10 which may remain may be trimmed off using scissors and discarded. The device 10 is then secured around the body portion or extremity 125 by attaching standard prong clips 115 in a similar manner as a conventional compression bandage, as needed.

Referring now to FIG. 5, a perspective view of the device 10 depicting hem portions 35, in accordance with an alternate embodiment of the present invention, is disclosed. In an alternate embodiment, an extending portion of the second elastic layer 30 may be provided which together with the first elastic layer 20 acts to form a hem 35 being sewn or adhesively bonded along each opposing parallel edge of the device 10, thereby covering and enclosing the aforementioned tori 100 and moldable wire 50 portions to provide added securement and protection.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the device 10, it would be installed as indicated in FIG. 1.

The method of utilizing the device 10 may be achieved by performing the following steps: acquiring a model of the device 10 having a desired height and width dimensions, compression ratio/direction, and wire 50 arrangement; unrolling the device 10; wrapping the device 10 about an extremity 125 such that each wire 50 is generally perpendicular to the longitudinal length of the extremity 125; positioning the device 10 such that the gauze substrate portion 110 is against the patient's skin 120; wrapping the device 10 around the extremity 125 a desired number of times and in a configuration as dictated by the situation; molding the wires 50 to conform to contour portions of the extremity 125 to create a shape that is salutary to the desired medical treatment being rendered; trimming off any remaining unused portion of the device 10 using scissors or an equivalent means; securing the device 10 around the body portion or extremity 125 by fastening the device 10 to itself using prong clips 115; and, allowing the compressive forces of the elastic layers 20, 30 and the stabilization forces of the wires 50 to provide a compressive bandage and splint for the injured patient 120 to which the device 10 is applied.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. An elongated elastic bandage, comprising:
   an elastic layer having a pair of longitudinal edges and a continuous length, said elastic layer comprising:
      a plurality of first threads substantially arranged in a first direction approximately perpendicular to said pair of longitudinal edges; and,
      a plurality of second threads substantially arranged in a second direction approximately parallel to said pair of longitudinal edges, said plurality of second threads being woven with said plurality of first threads;
   a plurality of moldable wires that are spaced apart and extend approximately parallel to each other, and wherein each one of said plurality of moldable wires is oriented approximately perpendicular to said pair of longitudinal edges; and,
   an adhesive to bind said moldable wires to a surface of said elastic layer.

2. A bandage, comprising:
   a first elongated elastic layer having a pair of first longitudinal edges, said first elongated elastic layer comprising:
      a first plurality of first threads substantially arranged in a first direction; and,
      a first plurality of second threads substantially arranged in a second direction and woven with said first plurality of first threads;
   a second elongated elastic layer connected to said first elongated layer and having a pair of second longitudinal edges approximately parallel to said pair of second longitudinal edges, said second elastic layer comprising:
      a second plurality of first threads substantially arranged in a third direction; and,
      a second plurality of second threads substantially arranged in a fourth direction and woven with said second plurality of first threads;
   a plurality of moldable wires located between said first elongated elastic layer and said second elongated elastic layer and which are spaced apart and arranged in a substantially parallel manner and wherein each one of said plurality of moldable wires is oriented approximately perpendicular to and extend fully between said pair of first longitudinal edges of said first elongated elastic layer; and,
   an adhesive disposed between said first elongated elastic layer and said second elongated elastic layer to bind said first elongated elastic layer and said second elongated elastic layer together and bind said plurality of moldable wires to said first elongated elastic layer and said second elongated elastic layer.

3. The bandage recited in claim 2, wherein said first plurality of first threads exhibit a stretching capability different than that of said first plurality of second threads.

4. The bandage recited in claim 2, wherein said second plurality of first threads exhibit a stretching capability different than that of said second plurality of second threads.

5. The bandage recited in claim 2, wherein said first plurality of first threads exhibit a different stretching capability than that of said second plurality of first threads.

6. The bandage recited in claim 2, wherein said first plurality of second threads exhibit a different stretching capability than that of said second plurality of second threads.

7. The bandage recited in claim 2, wherein said first direction is substantially parallel to said third direction.

8. The bandage recited in claim 2, wherein said second direction is substantially parallel to said fourth direction.

9. The bandage recited in claim 2, wherein each one of said plurality of moldable wires comprises a first end and an opposed second end, wherein said first end and said second end extend beyond said pair of first longitudinal edges of said first elongated elastic layer, and wherein each one of said plurality of moldable wires further comprises a torus-shaped member disposed on each of said first end and said second end.

10. The bandage recited in claim 2, wherein said pair of second longitudinal edges of said second elongated elastic layer extend beyond said pair of first longitudinal edges of said first elongated elastic layer, and wherein a portion of said second elongated elastic layer extending beyond said first elongated elastic layer is folded over said pair of first longitudinal edges of said first elongated elastic layer and connected to said first elongated elastic layer.

11. A bandage, comprising:
  a first elongated elastic layer having a pair of first longitudinal edges, said first elongated elastic layer comprising:
    a first plurality of first threads substantially arranged in a first direction; and,
    a first plurality of second threads substantially arranged in a second direction and woven with said first plurality of first threads;
  a second elongated elastic layer connected to said first elongated layer and having a pair of second longitudinal edges approximately parallel to said pair of second longitudinal edges, said second elastic layer comprising:
    a second plurality of first threads substantially arranged in a third direction; and,
    a second plurality of second threads substantially arranged in a fourth direction and woven with said second plurality of second threads;
  a plurality of moldable wires located between said first elongated elastic layer and said second elongated elastic layer, wherein said plurality of moldable wires are spaced apart and arranged approximately parallel to each other, and wherein each one of said plurality of moldable wires is oriented approximately perpendicular to and extend fully between said pair of first longitudinal edges of said first elongated elastic layer;
  a gauze pad connected to said first elongated elastic layer opposite said second elongated elastic layer; and,
  an adhesive disposed between said first elongated elastic layer and said second elongated elastic layer and surrounding said plurality of moldable wires to bind said first elongated elastic layer and said second elongated elastic layer together and bind said plurality of moldable wires between said first elongated elastic layer and said second elongated elastic layer.

12. The bandage recited in claim 11, further comprising an anti-bacterial non-stick ointment disposed on a surface of said gauze pad.

13. The bandage recited in claim 11, wherein each one of said first plurality of first threads exhibits a stretching capability different than that of each one of said first plurality of second threads.

14. The bandage recited in claim 11, wherein each one of said second plurality of first threads exhibits a stretching capability different than that of each one of said second plurality of second threads.

15. The bandage recited in claim 11, wherein each one of said first plurality of first threads exhibits a different stretching capability than that of each one of said second plurality of first threads.

16. The bandage recited in claim 11, wherein each one of said first plurality of second threads exhibits a different stretching capability than that of each one of said second plurality of second threads.

17. The bandage recited in claim 11, wherein said first direction is substantially parallel to said third direction.

18. The bandage recited in claim 11, wherein said second direction is substantially parallel to said fourth direction.

19. The bandage recited in claim 11, wherein each one of said plurality of moldable wires comprises a first end and an opposed second end, wherein said first end and said second end extend beyond said pair of first longitudinal edges of said first elongated elastic layer, and wherein each one of said plurality of moldable wires further comprises a torus-shaped member disposed on each of said first end and said second end.

20. The bandage recited in claim 11, wherein said pair of second longitudinal edges of said second elongated elastic layer extend beyond said pair of first longitudinal edges of said first elongated elastic layer, and wherein a portion of said second elongated elastic layer extending beyond said first elongated elastic layer is folded over said pair of first longitudinal edges of said first elongated elastic layer and connected to said first elongated elastic layer.

* * * * *